United States Patent
Kadin

[19]

[11] 4,075,343
[45] Feb. 21, 1978

[54] ANTI-ALLERGENIC 5-ALKOXYIMIDAZO[1,2-a]QUINOLINE-2-CARBOXYLIC ACIDS AND DERIVATIVES THEREOF

[75] Inventor: Saul B. Kadin, New London, Conn.

[73] Assignee: Pfizer Inc., New York, N.Y.

[21] Appl. No.: 722,429

[22] Filed: Sept. 13, 1976

[51] Int. Cl.² .................... A61K 31/47; C07D 471/04
[52] U.S. Cl. ................ 424/258; 260/283 S; 260/287 CF; 260/287 C; 260/288 CF; 260/288 R
[58] Field of Search .............. 260/287 C, 287 CF; 424/258

[56] References Cited
U.S. PATENT DOCUMENTS

| | | | |
|---|---|---|---|
| 2,421,693 | 6/1947 | Harriman | 260/288 CF |
| 3,454,579 | 7/1969 | Wright | 260/287 CF |
| 3,668,208 | 6/1972 | Baxter | 260/287 CF |

Primary Examiner—Donald G. Daus
Assistant Examiner—D. Wheeler
Attorney, Agent, or Firm—Connolly and Hutz

[57] ABSTRACT

A novel series of 5-alkoxyimidazo[1,2-a]quinoline-2-carboxylic acids and esters thereof of the formula (I)

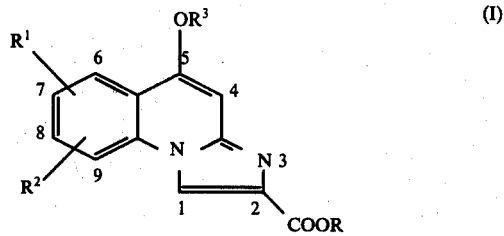

wherein R is hydrogen or alkyl having from one to five carbon atoms; each of $R^1$ and $R^2$ is hydrogen, alkyl having from one to five carbon atoms, alkoxy having from one to five carbon atoms, fluoro, chloro, bromo, methylthio or methylsulfinyl, with the proviso that when $R^1$ and $R^2$ are both bulky groups, i.e. branched chain alkyl or branched chain alkoxy, they are located on non-adjacent positions; and when $R^1$ and $R^2$ are taken together they form tetramethylene, 1,3-butadienyl, methylenedioxy or ethylenedioxy, each said group being attached to adjacent carbon atoms of the benzenoid ring; $R^3$ is alkyl having from one to five carbon atoms; and the pharmaceutically acceptable cationic salts of those compounds wherein R is hydrogen; compositions thereof; their use as antiallergy agents and certain intermediates for the preparation of said compounds of formula (I).

23 Claims, No Drawings

ANTI-ALLERGENIC 5-ALKOXYIMIDAZO[1,2-a]QUINOLINE-2-CARBOXYLIC ACIDS AND DERIVATIVES THEREOF

BACKGROUND OF THE INVENTION

1. Field of the Invention

This invention relates to imidazo [1,2-a]-quinoline-2-carboxylic acids and derivatives thereof and to their use as antiallergy agents. More particularly, it relates to 5-alkoxyimidazo[1,2-a]quinoline-2-carboxylic acids and derivatives thereof such as esters of the 2-carboxylic acid group, and derivatives of such compounds wherein the benzenoid ring bears up to two substituents; said compounds are useful as agents for the treatment of allergic reactions, especially allergic bronchial asthma; and to certain esters of 5-chloro(and 5-bromo)-imidazo[1,2-a]quinoline-2-carboxylic acids, useful as intermediates for the preparation of said antiallergy agents.

2. Description of the Prior Art

Allergic reactions, the symptoms resulting from an antigen-antibody interaction, manifest themselves in a wide variety of ways and in different organs and tissues. Common allergic disorders, for example, are allergic rhinitis, a condition characterized by seasonal or perennial sneezing, running nose, nasal congestion, with itching and congestion of eyes; hay fever, a variety of allergic rhinitis that results from hypersensitivity to grass polens; and bronchial asthma, one of the most disabling and debilitating of allergic reactions, a disease characterized by hyper-reactivity of the bronchi on exposure to various immunogenic or nonimmunogenic stimuli, resulting in bronchospasms with wheezing, short-lived paroxysms and widespread constriction of airway passages. The mechanical obstruction to airflow in airways is generally reversed by the use of bronchodilators, which provide symptomatic relief. In contrast, antiallergy agents prevent the release of mediators of anaphylaxis from tissue stores, thereby acting in a prophylactic manner to preclude elicitation of bronchoconstriction by the mediators.

Efforts to discover medicinal agents to alleviate the symptoms of the abnormal physiologic state have been extensive. As early as 1910, Matthews, *Brit. Med. J.*, 1, 441 (1910) reported the bronchodilator effects of epinephrine. Since then, Chen and Schmidt, *J. Pharmacol. Exper. Therap.*, 24, 339 (1924) reported the use of the alkaloid ephedrine as an orally efficacious bronchodilator with the same spectrum of activity as epinephrine. In 1940, Konzett, *Arch. Exp. Path. Pharmak.*, 197, 27 (1940) outlined the effects of the potent aerosol bronchodilator isoproterenol. Cullum et al., *Brit. J. Pharmacol. Exp.*, 35, 141 (1969) reported the pharmacology of salbutamol, a potent bronchodilator of prolonged duration, and active via both oral and aerosol administration. Many bronchodilator preparations contain theophylline. These are generally less potent than the sympathomimetic amines such as isoproterenol and salbutamol, and are ineffective in aerosol administration.

Recently, Cox and co-workers, *Adv. in Drug Res.*, 5, 115 (1970), described the pharmacology of the antiallergy agent, disodium cromoglycate [1,3-bis-(2-carboxy-cromon-5-yloxy)-2-hydroxypropane, Intal]. It is not a bronchodilator, but mediates its therapeutic effects by a unique mechanism of action involving inhibition of release of mediators of anaphylaxis and is administered prophylactically. It suffers from lack of oral efficacy and, for optimum results, is administered by inhalation as a solid inhalant. Further, although it is effective against anaphylaxis due to immunoglubin E (IgE), it is effective against anaphylaxis due to immunoglobulin G (IgG) only at high doses (60–70% protection at 100 and 300 mg./kg.).

Although the aforementioned agents represent outstanding contributions toward the treatment of asthma, many of them exert the undesired side effect of cardiac stimulation.

The first reference to the imidazo[1,2-a]quinoline ring systems appears to be that of U.S. Pat. No. 2,421,693 in which 3-acyl-2-keto-1,2-dihydroimidazo[1,2-a]quinolinium salts and the corresponding 3-alkyl, 3-aryl and 3-aralkyl compounds were claimed to be useful as magenta color formers. The chemistry of the known imidazo[1,2-a]quinolines was reviewed in "The Chemistry of Heterocyclic Compounds", A. Weissberger, Ed., Interscience Publishers, N.Y., 1961, pp. 518–521. The imidazo[1,2-a]quinoline-2-carboxylic acids and derivatives thereof have not previously been reported.

SUMMARY OF THE INVENTION

It has not been found that compounds of the formula (I)

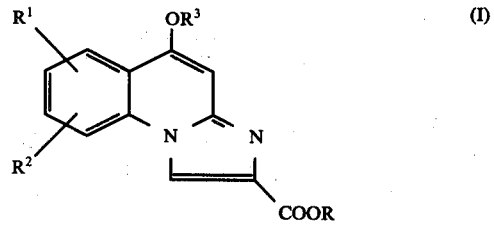

are valuable antiallergy agents, that is, agents which inhibit the release of mediators of anaphylaxis, in mammals, including man, and in this way preclude elicitation of bronchoconstriction by the mediators. They are not bronchodilators. They are, in contrast to disodium cromoglycate, of practical value against both IgE and IgG mediated anaphylaxis via the oral, intranasal and intraperitoneal routes of administration, and by inhalation. In formula (I), R is hydrogen or alkyl having from one to five carbon atoms; each of the benzenoid substituents, $R^1$ and $R^2$, is selected from the group consisting of hydrogen, alkyl having from one to five carbon atoms, alkoxy having from one to five carbon atoms, fluoro, chloro, bromo, methylthio and methylsulfinyl, with the priviso that when $R^1$ and $R^2$ are both branched chain alkyl or branched chain alkoxy, they are located on non-adjacent positions, and when taken together $R^1$ and $R^2$ are selected from the group consisting of tetramethylene, 1,3-butadienyl, methylenedioxy and ethylenedioxy, each said group being attached to adjacent carbon atoms of the benzenoid ring;

$R^3$ is alkyl having from one to five carbon atoms;

and the pharmaceutically acceptable cationic salts of those compounds wherein R is hydrogen.

While the compounds of formula (I) wherein R is said alkyl are active antiallergenic agents, they also serve as intermediates for the particularly preferred compounds of formula (I) wherein R is hydrogen.

By the term "pharmaceutically acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as triethylamine, tri-n-butylamine, piperidine, triethanolamine, diethylaminoethylamine, N,N'-dibenzylethylenediamine and pyrrolidine.

Compounds of particular interest to this invention are those of formula (I) wherein R is hydrogen and $R^1$, $R^2$ and $R^3$ are as tabulated below.

| $R^1$ | $R^2$ | $R^3$ |
|---|---|---|
| H | H | $CH_3$ |
| H | H | $C_2H_5$ |
| H | 7-F | $C_2H_5$ |
| H | 8-F | $CH_3$ |
| H | 7-Cl | $CH_3$ |
| H | 7-$CH_3$ | $C_2H_5$ |
| H | 7-$CH_3$ | $CH_3$ |
| H | 7-$C_2H_5$ | $CH_3$ |
| H | 7-$C_2H_5$ | $C_2H_5$ |
| 7-$CH_3O$ | 8-$CH_3O$ | $CH_3$ |

The 5-haloimidazo[1,2-a]quinoline-2-carboxylates of formula (II)

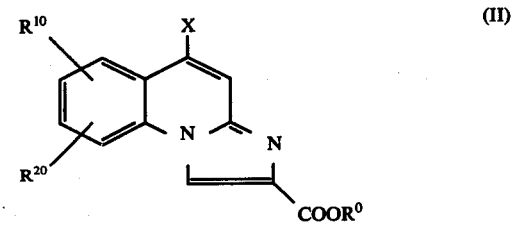

wherein X is chloro or bromo; $R^0$ is alkyl having from one to five carbon atoms; and $R^{10}$ and $R^{20}$ are each selected from the group consisting of hydrogen, alkyl having from one to five carbon atoms, alkoxy having from one to five carbon atoms and fluoro; with the proviso that when both of said $R^{10}$ and $R^{20}$ are branched chain alkyl or branched chain alkoxy they are located on non-adjacent positions; and when $R^{10}$ and $R^{20}$ are taken together they form a member of the group consisting of tetramethylene, 1,3-butadienyl, methylenedioxy and ethylenedioxy, each said group being attached to adjacent carbon atoms of the benzenoid ring; are valuable intermediates for preparation of the compounds of formula (I).

The antiallergy property of the compounds of this invention is evaluated by the passive cutaneous anaphylaxis (PCA) test (Ovary, J. Immun., 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

DETAILED DESCRIPTION OF THE INVENTION

The compounds of the invention are readily prepared by condensation of the appropriate 2-amino-4-alkoxyquinoline or 2-amino-4-chloro(or bromo)quinoline with the appropriate 3-halopyruvate ester, $ZCH_2COCOOR$, wherein Z is chloro or bromo and R is alky; preferred alkyl groups are those having from one to five carbon atoms. When the 2-amino-4-alkoxyquinolines are employed as starting materials, the products are the corresponding 5-alkoxyimidazo[1,2-a]quinoline-2-carboxylate esters of formula (I). When the 2-amino-4-haloquinolines are employed, the products are the corresponding 5-haloimidazo[1,2-a]quinoline-2-carboxylate esters (formula II) which are subsequently converted to the corresponding 5-alkoxy compounds of formula (I).

The condensation of 2-amino-4-alkoxyquinolines or 2-amino-4-haloquinolines with a 3-halopyruvate ester is carried out by heating a stoichiometric mixture of the appropriate reactants in the presence of a reaction inert solvent and, optionally, in the presence of a base such as, for example, potassium carbonate, sodium bicarbonate or triethylamine, at a temperature of from about 10° to 100° C. until cyclization is essentially complete, usually within 0.5 to 20 hours. At lower temperatures the reaction proceeds too slowly. Higher temperatures can be used but appear to offer no advantage. Examples of solvents which may be employed are methanol, ethanol, isopropanol, isoamylalcohol, acetone, 2-butanone, N,N-dimethylformamide, and dimethylsulfoxide. The esters of formulae (I) or (II) are isolated by standard methods. For example, when a base such as potassium carbonate is employed, the solvent may be removed by evaporation, the residue mixed with water, extracted with a water immiscible solvent such as chloroform or ethyl acetate, the extracts carbon treated, evaporated to dryness and the crude product purified if desired, e.g. by column chromatography on silica gel or by recrystallization from solvents such as ethanol, isopropanol, water, benzene, cyclohexane or mixtures thereof. When base is omitted from the reaction mixture, a precipitate usually forms which is filtered, partitioned between aqueous base and solvent such as chloroform and the extracts worked up as described above.

The compounds of formula (II) are readily converted to the corresponding compounds of formula (I) by replacement of the 5 chloro or 5-bromo substituent by treating with an excess of the appropriate alcohol, $R^3OH$, which also serves as solvent. This is preferably carried out in the presence of a catalytic amount of strong acid such as anhydrous hydrochloric, sulfuric or p-toluenesulfonic acid. Especially preferred is p-toluenesulfonic acid. While the reaction may be carried out over a wide range of temperature, a temperature of about 50°-100° C. is preferred. The reaction is ordinarily complete in about 5 to 24 hours. The desired product of formula (I) is isolated as described above.

The particularly preferred acids of formula (I) wherein R is hydrogen are conveniently prepared by hydrolysis, preferably alkaline hydrolysis, of the corresponding ester. The usual conditions comprise heating an aqueous mixture of the appropriate ester of formula (I) wherein R is said alkyl and an alkali such as, for example, sodium hydroxide, potassium hydroxide or sodium carbonate at a temperature of from about 50° to 100° C. for periods of up to four hours or until hydrolysis is essentially complete. The resulting aqueous solution or suspension is then acidified, for example with hydrochloric, sulfuric, phosphoric or acetic acid, to precipitate the desired acid of formula (I) which is isolated by filtration and further purified if desired by recrystallization, typically from solvents such as glacial acetic acid or N,N-dimethylformamide, The acids, in turn, serve as intermediates for the pharmaceutically acceptable cationic salts of this invention.

Salt formation is accomplished by reacting the appropriate acid with the appropriate metal salt, ammonia or amine. Examples of such salts are the carbonates, bicarbonates, acetates, hexanoates or hydroxides of cations such as sodium, potassium, ammonium, calcium, magnesium or aluminum. Examples of suitable amines are triethylamine, diethylaminoethylamine, pyrrolidine and N,N-dibenzylethylenediamine. Salt formation is ordinarily carried out in a suitable medium such as water, methanol or ethanol according to well known procedures. The salts are recovered by standard methods such as by filtration if they are insoluble in the medium, by evaporation of the solvent if they are soluble in the medium, or by precipitation by addition of a non-solvent for the salt.

Of the 3-halopyruvate ester reactants, ethyl 3-bromopyruvate is commercially available and many of the others are described in the literature. Those that are not described are conveniently prepared by esterifying 3-chloropyruvic acid or 3-bromopyruvic acid with the appropriate alcohol by conventional methods known to one skilled in the art or from the appropriate olefin by the procedure of Dmitriev et al., Chem. Abstr., 67, 54381b (1967).

The 2-amino-4-ether substituted quinoline reactants are readily prepared by reaction of the corresponding 2-amino-4-hydroxyquinoline with the appropriate alkyl ester of an arylsulfonic acid, such as an alkyl-p-toluenesulfonate or an alkyl ester of sulfuric acid. Alternatively, they are prepared by reaction of a metal salt--usually the sodium salt--of the appropriate 2-amino-4-hydroxyquinoline with the appropriate alkyl halide. The amino group is protected by acetylation, if necessary, to avoid alkylation.

Many of the requisite 2-amino-4-hydroxyquinolines are described in the literature. Those that are not described in the art are easily prepared by known procedures such as by reaction of the appropriate anilinium p-toluenesulfonate or benzenesulfonate with ethyl cyanoacetate as described by Hardman et al., J. Chem. Soc., 3878-3884 (1954).

Compounds of this invention wherein one or both of $R^1$ and $R^2$ is methylsulfinyl are readily prepared from the corresponding methylthio compounds by oxidation with an appropriate oxidizing agent such as hydrogen peroxide or a peracid such as m-chloroperbenzoic acid according to methods known to those skilled in the art. The methylthio compounds are, in turn, readily prepared by the reaction of the corresponding chloro or bromo compounds with sodium methyl mercaptide. Modifications of this method are obvious to those skilled in the art. For example, the methylthio ether can be made by in situ formation of the methyl mercaptide salt.

As mentioned above, the novel 5-haloimidazo[1,2-a]quinoline-2-carboxylic acid ester intermediates of formula (II) are prepared from the appropriate 2-amino-4-haloquinolines by condensation with the appropriate 3-halopyruvate ester.

The requisite 2-amino-4-chloroquinolines and 2-amino-4-bromoquinolines are conveniently obtained from the above mentioned 2-amino-4-hydroxyquinolines by reaction with a molar excess of halogenating agent such as phosphorus oxychloride, phosphorus oxybromide, phosphorus pentachloride or phosphorus tribromide. While the halogenation can be carried out over a wide range of temperature, a temperature of from about 50 to 150° C. is preferred. The reaction is ordinarily complete in from about 1 to 10 hours. The desired product is isolated by standard methods such as, for example, pouring the reaction mixture into water, adjusting to an alkaline pH and extraction with a water immiscible solvent such as chloroform or methylene chloride. The solvent is removed by evaporation and the product purified by recrystallization if desired.

As noted above, the 5-alkoxyimidazo[1,2-a]quinoline-2-carboxylic acids, salts and esters of this invention exhibit a significantly broader spectrum of activity than the commercial antiallergy agent disodium cromoglycate. While the latter compound is effective in inhibiting anaphylactic phenomena mediated by immunoglobulin E (IgE), it does not inhibit immunoglobulin G (IgG) mediated responses except at high doses. In contrast, the compounds of the invention are not only effective against reaginic (IgE) induced anaphylaxis, but also against IgG induced anaphylaxis.

The products of this invention and the pharmaceutically-acceptable cationic salts thereof are useful as prophylactic agents to inhibit or prevent the release of mediators of anaphylaxis (allergy, immediate hypersentitivity reactions) and the occurrence of allergic symptoms in mammals, and can be administered for such uses individually or as mixtures with other agents, for example, with theophyllidine or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds is sesame or peanut oil or aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds can be administered to asthmatic subjects suffering from bronchoconstriction by means of inhalators or other devices which permit the active compounds to come into direct contact with the constricted areas of the tissues of the subject. When administered by inhalation, the compositions can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for administration from a powder inhalation device. Compositions suitable for inhalation by means of a conventional nebulizer will comprise about 0.1 to about 1% by weight of active ingredient; and those for use in pressurized containers will comprise from about 0.5 to about 2% by weight of active ingredient. Compositions for use as powder inhalants can comprise ratios of active ingredient to diluent of from about 1:0.5 to about 1:1.5 by weight.

It is necessary that the active ingredient form a proportion of the compositions such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95, or an even higher percentage by weight of the active ingredient.

As regards the dosage regimen of the compounds of this invention, the physician will ultimately determine the dosage which will be most suitable for a particular individual, and it will vary with age, weight and response of the particular patient as well as with the nature and extent of the symptoms, the pharmacodynamic characteristics of the particular agent to be administered and the route of administration chosen. Generally, small doses will be administered initially, with a gradual increase in the dosage until optimum level is determined. It will often be found that when the composition is administered orally, larger quantities of the active ingredient will be required to produce the same level as produced by a small quantity administered parenterally.

Having full regard for the foregoing factors, it is considered that an effective daily oral dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively alleviate bronchoconstriction in human subjects. These values are illustrative and there may, of course, be individual cases where higher or lower dose ranges are merited.

When administered intravenously or by inhalation, the effective daily dose is from about 0.05 to about 400 mg. per day, and preferably from about 0.25 to 200 mg. per day, or at about 0.005 to 4 mg./kg. of body weight in single or divided doses.

The same two basic changes are present in cases of anaphylactic shock: (1) an increase in permeability of capillaries, and (2) contraction of smooth muscle. The increased capillary permeability is the result of antigenantibody interaction. It, and smooth muscle contraction, can be observed and readily measured. This increase in capillary permeability forms the basis of the PCA test.

The PCA test is a measure of the anti-allergic (especially antiasthmatic) activity of a compound. Compounds which inhibit a positive PCA test induced by the rat immunochemical counterpart of human immunoglobin E (IgE), or reagin, are considered to have anti-allergic activity (C. Mota, *Ann. N.Y. Acad. Sci.*, 103, 264 (1963). (Reagin is primarily immunoglobulin E [IgE] and is the principal immunoglobulin responsible for allergic asthma, anaphylaxis, hay fever, food sensitivities and certain manifestations of drug sensitivities). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions or a reagin mediated nature.

To put it another way, such compounds block the release of mediators resulting from the antigen-antibody (allergic) reaction as illustrated in the PCA test using rat homocytotropic antibody—a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170–210 g. Reaginic antiserum, rich in IgE antibodies is prepared according to Petillo et al., *Int. Arch. Allergy*, 44, 309 (1973). Hyperimmune antiserum rich in IgG antibodies to hen egg albumin is prepared according to Orange, et al., *J. Exptl. Med.*, 127, 767 (1968). Forty-eight hours prior to antigen challenge, the reaginic antiserum is injected intradermally (i.d.) into the shaved skin of a normal rat's back; 5 hours before challenge the hyperimmune antisera is similarly injected. At a third site 60 mcg. histamine dihydrochloride and 0.5 mcg. serotonin creatinine sulfate are injected i.d. just prior to antigen challenge as a check for antihistaminic, antiserotonin and unspecific types of blockage; the compounds of the instant invention or saline are then administered i.v. or i.p. and immediately followed by the challenge of 5 mg. egg albumen and 2.5 mg. Evans' Blue dye in saline. In the case or oral administration Evans' Blue dye and egg albumen are given five minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of 5 animals and compared to the saline treated controls. The difference is expressed as percent blockage due to the compound employed.

Compounds representative of those of the present invention are tested for antiallergy activity by the above-described procedure and the resulting activities are reported as the degree (%) inhibition of PCA. Intal, disodium cromoglycate, a commercial antiallergy agent, is included for comparison. The results are summarized in Table I.

Analysis: Calc'd for $C_{15}H_{14}N_2O_3$: C, 66.65; H, 5.22; N, 10.37. Found: C, 65.90; H, 5.19; N, 10.14.

The mass spectrum showed a peak at M/e 270.

EXAMPLE 2

Ethyl 5-Ethoxy-7-fluoroimidazo[1,2-a]quinoline-2-carboxylate

In a single-necked flask were combined, 2.1 g. (0.010 mole) of 2-amino-4-ethoxy-6-fluoroquinoline, 2.1 g. (0.011 mole) ethyl bromopyruvate and 30 ml. of acetone. The mixture was refluxed for two hours, cooled to

TABLE I

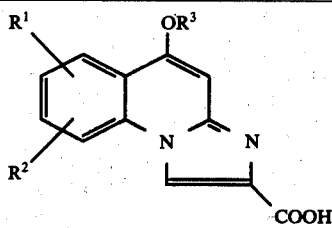

| | | | INHIBITION OF PCA | | | | | |
|---|---|---|---|---|---|---|---|---|
| | | | Ig E | | | Ig G | | |
| $R^1$ | $R^2$ | $R^3$ | mg./kg. | % | Administration | mg./kg. | % | Administration |
| H | H | $CH_3$ | 0.3 | 78 | i.v. | — | — | — |
| | | | 3.0 | 90 | oral | — | — | — |
| H | H | $C_2H_5$ | 3.0 | 89 | i.v. | 3.0 | 87 | i.v. |
| H | 7-$CH_3O$ | $CH_3$ | 30 | 95 | i.v. | 30 | 48 | i.v. |
| H | 7-F | $C_2H_5$ | 3.0 | 96 | i.v. | — | — | — |
| H | 8-F | $CH_3$ | 3.0 | 96 | i.v. | 3.0 | 69 | i.v. |
| 7-$CH_3$ | 8-$CH_3$ | $CH_3$ | 30 | 72 | i.p. | 30 | 78 | i.p. |
| H | 7-Cl | $CH_3$ | 30 | 91 | i.p. | 30 | 93 | i.p. |
| H | 7-Cl | $C_2H_5$ | 30 | 76 | i.p. | 30 | 95 | i.p. |
| H | 7-$CH_3$ | $C_2H_5$ | 3.0 | 100 | i.v. | 3.0 | 76 | i.v. |
| H | 7-$CH_3$ | $CH_3$ | 10 | 100 | i.v. | 10 | 80 | i.v. |
| H | 7-$CH_3O$ | $C_2H_5$ | 30 | 100 | i.v. | 30 | 75 | i.v. |
| | | | 3.0 | 40 | i.v. | | | |
| 8,9-$(CH_2)_4$— | | $C_2H_5$ | 30 | 11 | i.p. | 30 | 61 | i.p. |
| H | 7-$C_2H_5$ | $CH_3$ | 10 | 78 | i.v. | 10 | 74 | i.v. |
| H | 7-$C_2H_5$ | $C_2H_5$ | 10 | 98 | i.v. | 10 | 52 | i.v. |
| 7-$CH_3O$ | 8-$CH_3O$ | $CH_3$ | 0.3 | 100 | i.v. | 0.3 | 83 | i.v. |
| Disodium Cromoglycate* | | | 100 | 100 | i.v. | | | |
| | | | 100 | 0 | oral | | | |
| | | | 30 | 99[2] | i.v. | | | |
| | | | 10 | 89[3] | i.v. | | | |
| | | | 3 | 78 | i.v. | | | |
| | | | 1 | 56[8] | i.v. | | | |
| | | | 0.3 | 29[5] | i.v. | | | |
| | | | 0.1 | 19[3] | i.v. | | | |

*The superscripts indicate a particular value is an average of two or more determinations.

EXAMPLE 1

Ethyl 5-Methoxyimidazo[1,2-a]quinoline-2-carboxylate

To 75 ml. of acetone was added 3.5 g. (0.20 mole) of 2-amino-4-methoxyquinoline, 4.3 g. (0.22 mole) of ethyl bromopyruvate and 3.0 g. (0.20 mole) potassium carbonate. The resulting mixture was heated at reflux for 5.5 hours and the resulting dark slurry allowed to stand at room temperature overnight. The solvent was removed by evaporation in vacuo and 200 ml. of water added to the residue to afford a gummy precipitate. This was extracted twice with 200 ml. portions of ethyl acetate, the extracts dried over anhydrous sodium sulfate, decolorized with active carbon (Darco), filtered and the solvent removed in vacuo to afford 3.5 g. of crude product. Filtration of the aqueous phase from the extraction step afforded another 1.0 g. of crude material. The combined crops were recrystallized from 100 ml. of 1:1 (by volume) isopropanol-water to afford 900 mg. of the title compound, M.P. 175°–176.5° C.

room temperature and the precipitated solid removed by filtration. The solid was partitioned between chloroform and 1N aqueous potassium hydroxide, the organic layer dried over magnesium sulfate and evaporated to dryness to yield 1.7 g. of crude product. This was dissolved in a small amount of chloroformethanol (95:5 v/v) and chromatographed on a column of 50 g. of 60–200 mesh silica gel (J. T. Baker Co.) eluting with the same solvent. Fractions of 50 ml. each were taken when ultraviolet light absorbing material began to come off the column. Fractions 1 through 8 were combined and evaporated to dryness in vacuo to afford 750 mg. of the title compound as a white solid, which upon crystallization from isopropanol melted at 213.5°–214.5° C.

Analysis: Calc'd for $C_{16}H_{15}N_2O_3F$: C, 63.56; H, 5.00; N, 9.27. Found: C, 63.46; H, 5.11; N, 9.54.

EXAMPLE 3

Ethyl 5,7,8-Trimethoxyimidazo[1,2-a]quinoline-2-carboxylate

To 50 ml. of N,N-dimethylformamide was added 5.2 g. (0.022 mole) of 2-amino-4,6,7-trimethoxyquinoline, and 3.38 g. (0.0244 mole) potassium carbonate. To the resulting slurry was added dropwise over 15 minutes 4.76 g. (0.0244 mole) ethyl bromopyruvate. The reaction mixture was stirred at room temperature 1.75 hours, during which the mixture became orange and a solid precipitated. Upon pouring onto 400 ml. of cold water a solid material formed which was filtered, dried, then dissolved in the minimum amount of chloroform. The solution was charged onto a column made up of 100 g. of silica gel in chloroform and elution with chloroform started. After 200 ml. of eluate was collected, elution with chloroform/ethanol (98:2 v/v) was started and 200 ml. fractions were collected. Fractions 1 through 4 were combined and evaporated to dryness to afford 3.0 g. of product. Recrystallization from benzene/cyclohexane yielded 2.7 g. of colorless solid, M.P. 195°–197° C.

Analysis: Calc'd for $C_{17}H_{18}N_2O_5$: C, 61.86; H, 5.49; N, 8.48. Found: C, 61.79; H, 5.52; N, 8.50.

EXAMPLE 4

The following compounds are similarly prepared from the appropriate reactants by the procedures of Example 1–3.

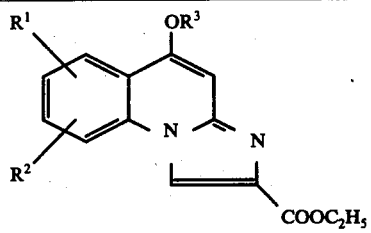

| $R^1$ | $R^2$ | $R^3$ | M.P., °C. | Calc'd C | H | N | Found C | H | N |
|---|---|---|---|---|---|---|---|---|---|
| H | 7-OCH$_3$ | CH$_3$ | 206–207.5 | 63.99 | 5.37 | 9.32 | 63.71 | 5.64 | 9.13 |
| H | 8-F | CH$_3$ | 241–243 | 62.49 | 4.54 | 9.71 | 62.27 | 4.65 | 9.79 |
| H | H | C$_2$H$_5$ | 170–171 | 67.59 | 5.67 | 9.85 | 67.31 | 5.76 | 9.78 |
| H | 8-CH$_3$ | CH$_3$ | 156–158 | 67.59 | 5.67 | 9.85 | 68.12 | 5.82 | 9.63 |
| H | 7-CH$_3$ | CH$_3$ | 179–180 | 67.59 | 5.67 | 9.85 | 67.34 | 5.62 | 9.78 |
| H | 7-CH$_3$ | C$_2$H$_5$ | 185–186 | 68.44 | 6.08 | 9.39 | 68.24 | 6.04 | 9.19 |
| H | 7-C$_2$H$_5$ | CH$_3$ | 167–168 | 68.44 | 6.08 | 9.39 | 68.05 | 6.10 | 9.29 |
| H | 7-C$_2$H$_5$ | C$_2$H$_5$ | 181–183 | 69.21 | 6.45 | 8.97 | 68.76 | 6.38 | 8.92 |
| H | 7-Cl | CH$_3$ | 230–231 | 59.12 | 4.30 | 9.19 | 59.01 | 4.37 | 9.11 |
| H | 7-Cl | C$_2$H$_5$ | 208–210 | 60.28 | 4.74 | 8.78 | 60.16 | 4.77 | 8.89 |
| 7-CH$_3$ | 8-CH$_3$ | CH$_3$ | 193–194 | 68.44 | 6.08 | 9.39 | 68.47 | 6.07 | 9.26 |
| 8,9-(CH$_2$)$_4$— | | C$_2$H$_5$ | 142–144 | 70.98 | 6.55 | 8.28 | 70.80 | 6.53 | 8.12 |
| H | 7-OCH$_3$ | C$_2$H$_5$ | 177–179 | 64.96 | 5.77 | 8.91 | 64.55 | 5.75 | 8.71 |

EXAMPLE 5

Ethyl 5-Chloroimidazo[1,2-a]quinoline-2-carboxylate

To 200 ml. of N,N-dimethylformamide is added 17.9 g. (0.10 mole) of 2-amino-4-chloroquinoline and 15.2 g. (0.11 mole) potassium carbonate. To this stirred slurry is added dropwise over 20 minutes 21.5 g. (0.11 mole) of ethyl bromopyruvate and the resulting mixture stirred for two hours. The solvent is then removed in vacuo and the residue was triturated with water, extracted three times with ethyl acetate, the extracts dried over anhydrous sodium sulfate, carbon treated, filtered and the solvent evaporated to afford the title compound. Further purification is achieved by crystallization or silica gel chromatography.

The following compounds are similarly prepared from the appropriate reactants:

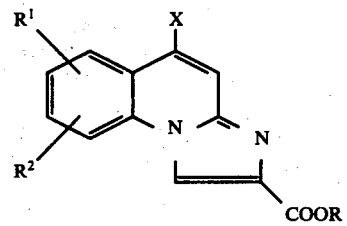

| X | R | $R^1$ | $R^2$ |
|---|---|---|---|
| Cl | C$_2$H$_5$ | H | 7-OCH$_3$ |
| Cl | CH$_3$ | H | 9-CH$_3$ |
| Cl | C$_2$H$_5$ | 6-CH$_3$ | 8-CH$_3$ |
| Br | C$_2$H$_5$ | 6-neo-C$_5$H$_{11}$ | 9-neo-C$_5$H$_{11}$ |
| Cl | CH$_3$ | H | 7-O-n-C$_5$H$_{11}$ |
| Br | n-C$_5$H$_{11}$ | 7-O-t-C$_4$H$_9$ | 9-CH$_3$ |
| Br | C$_2$H$_5$ | 6-O-t-C$_4$H$_9$ | 9-O-t-C$_4$H$_9$ |
| Cl | C$_2$H$_5$ | | 7,8-OCH$_2$O— |
| Cl | C$_2$H$_5$ | | 7,8-OCH$_2$CH$_2$O— |
| Cl | C$_2$H$_5$ | | 7,8-CH=CH—CH=CH— |
| Cl | i-C$_5$H$_{11}$ | | 8,9-(CH$_2$)$_4$— |
| Br | n-C$_3$H$_7$ | H | H |
| Br | n-C$_5$H$_{11}$ | H | H |
| Cl | n-C$_3$H$_7$ | 6-F | 8-F |
| Cl | CH$_3$ | 7-OCH$_3$ | 8-OCH$_3$ |

EXAMPLE 6

Ethyl 5-n-Butoxyimidazo[1,2-a]quinoline-2-carboxylate

A mixture of ethyl 5-chloroimidazo[1,2-a]quinoline-2-carboxylate 2.75 g. (0.01 mole) and 40 mg. of p-toluenesulfonic acid monohydrate in 150 ml. of n-butanol is heated at 100° C. for 18 hours. The butanol is then removed under reduced pressure. The residue is dissolved in a small amount of chloroform and chromatographed on a silica gel column. The fractions containing the title compound are combined and evaporated to dryness. The product can be further purified by crystallization.

EXAMPLE 7

The following compounds of formula (I) are prepared from the appropriate 2-amino-(4-substituted)-quinolines and the appropriate 3-halopyruvate of formula ZCH$_2$COCOOR by the procedures of Examples 1-3 and EXamples 5-6.

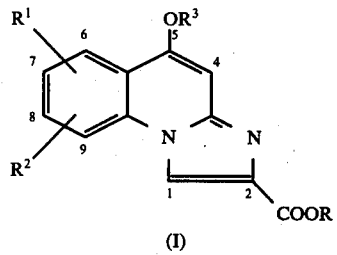

(I)

| Z | R | R$^1$ | R$^2$ | R$^3$ | Procedure |
|---|---|-------|-------|-------|-----------|
| Cl | CH$_3$ | H | H | n-C$_3$H$_7$ | Ex. 3 |
| Cl | n-C$_3$H$_7$ | H | H | n-C$_4$H$_9$ | Ex. 5-6 |
| Cl | n-C$_5$H$_{11}$ | H | H | n-C$_5$H$_{11}$ | Ex. 1 |
| Cl | i-C$_5$H$_{11}$ | H | H | i-C$_5$H$_{11}$ | Ex. 3 |
| Cl | CH$_3$ | H | 9-CH$_3$ | CH$_3$ | Ex. 5-6 |
| Cl | -C$_2$H$_5$ | H | 9-neo-C$_5$H$_{11}$ | i-C$_3$H$_7$ | Ex. 2 |
| Cl | neo-C$_5$H$_{11}$ | 7-i-C$_3$H$_7$ | 9-i-C$_3$H$_7$ | CH$_3$ | Ex. 2 |
| Cl | CH$_3$ | 6-t-C$_4$H$_9$ | 9-t-C$_4$H$_9$ | n-C$_4$H$_9$ | Ex. 3 |
| Br | C$_2$H$_5$ | 6-neo-C$_5$H$_{11}$ | 9-neo-C$_5$H$_{11}$ | C$_2$H$_5$ | Ex. 5-6 |
| Br | C$_2$H$_5$ | 6-CH$_3$ | 8-CH$_3$ | CH$_3$ | Ex. 5-6 |
| Br | C$_2$H$_5$ | 6-CH$_3$O | 8-CH$_3$O | CH$_3$ | Ex. 1 |
| Br | CH$_3$ | H | 7-n-C$_5$H$_{11}$O | n-C$_5$H$_{11}$ | Ex. 5-6 |
| Br | n-C$_3$H$_7$ | H | 9-t-C$_4$H$_9$O | CH$_3$ | Ex. 1 |
| Br | n-C$_5$H$_{11}$ | 7-t-C$_4$H$_9$O | 9-CH$_3$ | C$_2$H$_5$ | Ex. 5-6 |
| Br | C$_2$H$_5$ | 6-C$_2$H$_5$O | 9-C$_2$H$_5$O | C$_2$H$_5$ | Ex. 3 |
| Br | C$_2$H$_5$ | 6-t-C$_4$H$_9$O | 9-t-C$_4$H$_9$O | CH$_3$ | Ex. 5-6 |
| Br | C$_2$H$_5$ | 7,8-O-CH$_2$-O- | | CH$_3$ | Ex. 3 |
| Br | CH$_3$ | H | 7-Br | CH$_3$ | Ex. 1 |
| Br | C$_2$H$_5$ | 7-Cl | 8-Cl | CH$_3$ | Ex. 1 |
| Cl | CH$_3$ | 7,8-O-CH$_2$-O- | | neo-C$_5$H$_{11}$ | Ex. 1 |
| Cl | C$_2$H$_5$ | H | 7-CH$_3$SO | CH$_3$ | Ex. 2 |
| Br | n-C$_4$H$_9$ | 7-CH$_3$SO | 8-CH$_3$SO | C$_2$H$_5$ | Ex. 2 |
| Br | n-C$_3$H$_7$ | H | 7-CH$_3$S | CH$_3$ | Ex. 2 |
| Br | CH$_3$ | H | 9-CH$_3$S | CH$_3$ | Ex. 3 |
| Br | C$_2$H$_5$ | 6-Br | 9-Br | CH$_3$ | Ex. 3 |
| Br | C$_2$H$_5$ | 7-Br | 9-Br | C$_2$H$_5$ | Ex. 3 |
| Br | C$_2$H$_5$ | 8-Cl | 9-Cl | CH$_3$ | Ex. 3 |
| Br | C$_2$H$_5$ | 7-CH$_3$S | 8-CH$_3$S | CH$_3$ | Ex. 3 |
| Br | C$_2$H$_5$ | H | 9-Br | C$_2$H$_5$ | Ex. 3 |
| Br | C$_2$H$_5$ | 6-CH$_3$O | 9-CH$_3$O | CH$_3$ | Ex. 3 |
| Br | C$_2$H$_5$ | 7-n-C$_4$H$_9$O | 8-n-C$_4$H$_9$O | C$_2$H$_5$ | Ex. 3 |
| Br | C$_2$H$_5$ | 7-n-C$_3$H$_7$O | 8-Br | CH$_3$ | Ex. 3 |
| Br | n-C$_3$H$_7$ | 6-F | 8-F | CH$_3$ | Ex. 1 |
| Br | C$_2$H$_5$ | 7-CH$_3$S | 8-Cl | n-C$_3$H$_7$ | Ex. 1 |
| Br | C$_2$H$_5$ | 7-CH$_3$SO | 8-Cl | n-C$_3$H$_7$ | Ex. 1 |
| Br | C$_2$H$_5$ | 7,8-OCH$_2$CH$_2$O— | | CH$_3$ | Ex. 5-6 |
| Br | C$_2$H$_5$ | 7,8-CH=CH—CH=CH— | | CH$_3$ | Ex. 5-6 |
| Br | CH$_3$ | 7,8-OCH$_2$CH$_2$O— | | n-C$_5$H$_{11}$ | Ex. 2 |
| Br | C$_2$H$_5$ | H | 7-CH$_3$O | n-C$_5$H$_{11}$ | Ex. 5-6 |
| Br | C$_2$H$_5$ | H | 7-C$_2$H$_5$O | neo-C$_5$H$_{11}$ | Ex. 2 |
| Cl | CH$_3$ | H | 8-CH$_3$O | n-C$_4$H$_9$ | Ex. 3 |
| Cl | CH$_3$ | 7-CH$_3$O | 8-CH$_3$O | i-C$_5$H$_{11}$ | Ex. 3 |
| Br | C$_2$H$_5$ | 6-CH$_3$ | 9-CH$_3$O | t-C$_4$H$_9$ | Ex. 3 |
| Br | C$_2$H$_5$ | 6-CH$_3$O | 9-CH$_3$O | CH$_3$ | Ex. 1 |
| Br | C$_2$H$_5$ | 7-CH$_3$O | 9-CH$_3$O | C$_2$H$_5$ | Ex. 1 |
| Br | CH$_3$ | 7-CH$_3$SO | 8-CH$_3$S | n-C$_3$H$_7$ | Ex. 1 |
| Br | CH$_3$ | 7-Cl | 8-CH$_3$S | n-C$_4$H$_9$ | Ex. 3 |
| Br | i-C$_5$H$_{11}$ | 8,9-(CH$_2$)$_4$— | | n-C$_3$H$_7$ | Ex. 5-6 |

EXAMPLE 8

5-Methoxyimidazo[1,2-a]quinoline-2-carboxylic Acid

To 15 ml. of 1N aqueous potassium hydroxide was added 500 mg. (1.8 mmoles) of ethyl 5-methoxyimidazo[1,2-a]quinoline-2-carboxylate and the mixture was heated on the steam bath at 95° C. for 30 minutes to obtain a clear yellow solution. The solution was cooled to room temperature, acidified with acetic acid, filtered and the damp solid was recrystallized from 15 ml. of glacial acetic acid to afford 315 mg. (63%) of colorless crystals, M.P. 254° C. (dec.). The mass spectrum showed a peak at M/e 242.

Analysis: Calc'd for C$_{13}$H$_{10}$N$_2$O$_3$.1/2 CH$_3$COOH: C, 61.76; H, 4.44; N, 10.29. Found: C, 61.05; H, 4.13; N, 10.82.

EXAMPLE 9

The products obtained in Examples 2-4 were hydrolyzed by the procedure of Example 8 to provide the following imidazo[1,2-a]quinoline-2-carboxylic acids:

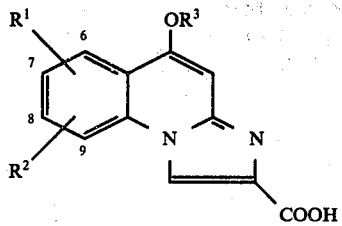

| R¹ | R² | R³ | M.P. °C. | Approx. M. W. by Mass Spectrum | % Yield |
|---|---|---|---|---|---|
| H | 7-F | $C_2H_5$ | 270(dec.) | 274 | 70 |
| 7-$CH_3O$ | 8-$CH_3O$ | $CH_3$ | 257(dec.) | 302 | 95 |
| H | 7-$CH_3O$ | $CH_3$ | 240–242 | 272 | 66 |
| H | 8-F | $CH_3$ | 265-7(dec.) | 260 | 76 |
| H | H | $C_2H_5$ | 268(dec.) | 256 | 89 |
| H | 8-$CH_3$ | $CH_3$ | 257–259 | 256 | 70 |
| H | 7-$CH_3$ | $CH_3$ | 250(dec.) | 256 | 100 |
| H | 7-$CH_3$ | $C_2H_5$ | 253–5(dec.) | 270 | 100 |
| H | 7-$C_2H_5$ | $CH_3$ | 249(dec.) | 270 | 100 |
| H | 7-$C_2H_5$ | $C_2H_5$ | 259(dec.) | 284 | 80 |
| H | 7-Cl | $CH_3$ | 265(dec.) | 276 | 81 |
| H | 7-Cl | $C_2H_5$ | 265(dec.) | 290 | 44 |
| 7-$CH_3$ | 8-$CH_3$ | $CH_3$ | 269–271 (dec.) | 270 | 100 |
| 8,9-$(CH_2)_4$— | | $C_2H_5$ | 249(dec.) | 310 | 100 |
| H | 7-$CH_3O$ | $C_2H_5$ | 251-3(dec.) | 286 | 100 |

EXAMPLE 10

When each of the products obtained in Example 7 is hydrolyzed by the procedure of Example 8 the corresponding imidazo[1,2-a]quinoline-2-carboxylic acid is obtained.

EXAMPLE 11

Salt Formation

The products of Examples 8–10 are converted to the sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 12

Injectable Preparation

One hundred grams of 5-methoxyimidazo[1,2-a]quinoline-2-carboxylic acid are intimately mixed and ground with 250 grams of sodium ascorbate. The ground, dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

EXAMPLE 13

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient 5,7,8-trimethoxyimidazo[1,2-a]quinoline-2-carboxylate, sodium salt, to provide tablets containing 20, 100 and 250 mg. of active ingredient per tablet. The compositions are each compressed into tablets, each weighing 360 mg., by conventional means.

EXAMPLE 14

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 5-ethoxy-7-fluoroimidazo[1,2-a]quinoline-2-carboxylic acid to provide capsules containing 10, 25 and 50 mg. hard gelatin capsules in the amount of 350 mg. per capsule.

In like manner, capsules containing 2.0 mg. and 6.0 mg. of active ingredient, and having 300 mg. of the following blends per capsule are prepared:

| Ingredients | Weight mg./capsule |
|---|---|
| Drug | 2.00 |
| N-Methylglucamine | 18.00 |
| Lactose, anhydrous | 241.20 |
| Corn starch, anhydrous | 30.00 |
| *Talc | 8.80 |

| Ingredients | Weight mg./capsule |
|---|---|
| Drug | 6.00 |
| N-Methylglucamine | 18.00 |
| Lactose, anhydrous | 237.20 |
| Corn starch, anhydrous | 30.00 |
| *Talc | 8.80 |

*Talc added before encapsulation

EXAMPLE 15

Solution

A solution of 5-methoxy-8-fluoroimidazo[1,2-a]quinoline-2-carboxylic acid is prepared with the following composition:

| | | |
|---|---|---|
| Effective ingredient | 6.04 | grams |
| Magnesium chloride hexahydrate | 12.36 | grams |
| Monoethanolamine | 8.85 | ml. |
| Propylene glycol | 376.00 | grams |
| Water, distilled | 94.00 | ml. |

The resultant solution has a concentration of effective ingredient of 10 mg./ml. and is suitable for parenteral, and especially for intramuscular administration.

EXAMPLE 16

An aqueous solution of 5-ethoxyimidazo[1,2-a]quinoline-2-carboxylic acid sodium salt (containing 3 mg. of drug per ml. of solution) is placed in a standard nebulizer such as is available from the Vaponephrine Co., Edison, N.J. The solution is sprayed under an air pressure of 6 lbs. per square inch into a closed 8 inches × 8 inches × 12 inches plastic container for six minutes. The container has four openings to accomodate the heads of four rats. Four rats are exposed to the drug simultaneously with only their heads coming in contact with aerosol. The results are evaluated as per the PCA reaction test procedure described above.

EXAMPLE 17

Aerosol Suspension

A mixture of 5-methoxyimidazo[1,2-a]quinoline-2-carboxylic acid (antiallergy agent) and the other ingredients under (a) in the examples below are micronized to a particle size of 1 to 5 microns in a ball mill. The resulting slurry is then placed in a container equipped with a valve and propellant (b) introduced by pressure filling through the valve nozzle to a gauge pressure of approximately 35–40 pounds per square inch at 20° C.

| Suspension A | Percent, weight |
|---|---|
| (a) Antiallergy agent | 0.50 |
| Isopropyl myristate | 0.10 |
| Ethanol | 26.40 |
| (b) 60–40% mixture of 1,2-dichlorotetrafluoroethane-1-chloropentafluoroethane | 73.00 |
| Suspension B | Percent, weight |
| (a) Antiallergy agent | 2.00 |
| Ethanol | 26.50 |
| (b) 60–40% mixture of 1,2-dichlorotetrafluoroethane-1-chloropentafluoroethane | 71.50 |

PREPARATION A

2-Amino-4-hydroxyquinolines

The appropriate aniline p-toluenesulfonate and ethyl cyanoacetate are combined in equimolar quantities and heated at 225° to 260° C. until a melt resulted (higher temperatures are used if necessary to achieve a melt). The temperature of the melt is lowered to 240°–250° C. and heating continued for one hour. The hot melt is poured into ice-cold chloroform (about 1 to 1.5 liters per mole of aniline reactant) and the mixture stirred for one hour. The solid is filtered off, added to water-ethanol (1 liter of 1:1 per mole of aniline reactant) at 45°–50° C. and the solution made basic with ammonium hydroxide. The solid is separated by filtration and recrystallized from a suitable solvent such as isopropanol.

The following compounds are prepared in this manner.

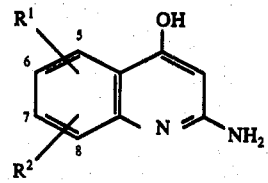

| $R^1$ | $R^2$ |
|---|---|
| H | H |
| H | 6-F |
| 6-CH$_3$O | 7-CH$_3$O |
| H | 6-CH$_3$O |
| H | 7-F |
| H | 7-CH$_3$ |
| H | 6-CH$_3$ |
| H | 6-C$_2$H$_5$ |
| H | 6-Cl |
| 6-CH$_3$ | 7-CH$_3$ |
|  | 7,8-(CH$_2$)$_4$— |
| H | 8-CH$_3$ |
| H | 8-neo-C$_5$H$_{11}$ |
| 6-i-C$_3$H$_7$ | 8-i-C$_3$H$_7$ |
| 5-neo-C$_5$H$_{11}$ | 8-neo-C$_5$H$_{11}$ |
| 5-CH$_3$ | 7-CH$_3$ |
| 5-CH$_3$O | 7-CH$_3$O |
| H | 6-n-C$_5$H$_{11}$O |
| H | 8-t-C$_4$H$_9$O |

-continued

| $R^1$ | $R^2$ |
|---|---|
| 6-t-C$_4$H$_9$O | 8-CH$_3$ |
| 5-C$_2$H$_5$O | 8-C$_2$H$_5$O |
| 5-t-C$_4$H$_9$O | 8-t-C$_4$H$_9$O |
|  | 6,7-OCH$_2$O— |
| H | 6-Br |
| 6-Cl | 7-Cl |
|  | 6,7-OCH$_2$CH$_2$O— |
| H | 6-CH$_3$SO |
| 6-CH$_3$SO | 7-CH$_3$SO |
| H | 6-CH$_3$S |
| H | 8-CH$_3$S |
| 5-Br | 8-Br |
| 6-Br | 8-Br |
| 7-Cl | 8-Cl |
| 6-CH$_3$S | 7-CH$_3$S |
| H | 8-Br |
| 5-CH$_3$O | 8-CH$_3$O |
| 6-n-C$_4$H$_9$O | 7-n-C$_4$H$_9$O |
| 6-n-C$_3$H$_7$O | 7-Br |
| 5-F | 7-F |
| 6-CH$_3$S | 7-Cl |
| 6-CH$_3$SO | 7-Cl |
|  | 6,7-CH=CH—CH=CH— |
| H | 6-C$_2$H$_5$O |
| H | 7-CH$_3$O |
| 5-CH$_3$ | 8-CH$_3$O |
| 6-CH$_3$O | 8-CH$_3$O |
| 6-CH$_3$SO | 7-CH$_3$S |
| 6-Cl | 7-CH$_3$S |

PREPARATION B

Ethers of 2-Amino-4-hydroxyquinoline via Esters of p-Toluenesulfonic Acid

A mixture of the appropriate 2-amino-4-hydroxyquinoline and the appropriate lower alkyl p-toluenesulfonate (10 to 20% molar excess) in xylene (from about 1–2 liters per mole of quinoline compound) is heated at reflux for 4–5 hours. It is then cooled, filtered and the filter cake washed with xylene. The solid is slurried in 3N KOH for 15–20 minutes and then filtered. The filter cake is washed with water, dried and recrystallized from a suitable solvent.

The 2-amino-4-lower-alkoxyquinoline reactants used in the preceding examples are prepared by this general procedure.

PREPARATION C

2-Amino-4-chloroquinolines and 2-Amino-4-bromoquinolines

The appropriate 2-amino-4-hydroxyquinoline and a molar excess of phosphorous oxychloride or phosphorous oxybromide are heated at 100°–120° C. for 2–6 hours, then poured into cold water, made alkaline by addition of a base such as aqueous sodium hydroxide solution and extracted with chloroform or methylene chloride. The extracts are evaporated to dryness and the residue recrystallized from a suitable solvent such as ethanol, isopropanol, benzene or ethyl acetate. The following compounds are prepared in this manner:

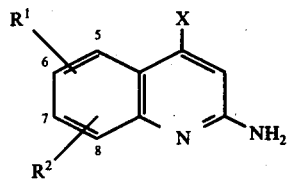

| X | R¹ | R² |
|---|----|----|
| Cl | H | H |
| Cl | H | 6-CH₃O |
| Cl | H | 8-CH₃ |
| Cl | 5-CH₃ | 7-CH₃ |
| Br | 5-neo-C₅H₁₁ | 8-neo-C₅H₁₁ |
| Cl | H | 6-n-C₅H₁₁O |
| Br | 6-t-C₄H₉O | 8-CH₃ |
| Br | 5-t-C₄H₉O | 8-t-C₄H₉O |
| Cl | | 6,7-OCH₂O— |
| Cl | | 6,7-OCH₂CH₂O— |
| Cl | | 6,7-CH=CH—CH=CH— |
| Cl | | 7,8-(CH₂)₄— |
| Br | H | H |
| Cl | 5-F | 7-F |
| Cl | 6-CH₃O | 7-CH₃O |

PREPARATION D

2-Amino-4-methoxy-6,7-dimethylthioquinoline

A solution of the sodium salt of methylmercaptan (0.09 mole) in N,N-dimethylformamide (50 ml.) is prepared by bubbling methylmercaptan into a mixture of sodium hydride (3.36 g. of 57% NaH) in N,N-dimethylformamide (100 ml.). The reaction mixture is cooled by means of an ice-bath until the reaction is complete.

The sodium methylmercaptide solution is then added dropwise to a mixture of 2-amino-4-methoxy-6,7-dichloroquinoline (0.04 mole) in N,N-dimethylformamide (50 ml.) cooled in an ice-bath. The mixture is stirred for one hour and then removed from the ice-bath and stirred for an additional two hours. The reaction mixture is poured into water (600 ml.) and the resulting mixture thoroughly stirred. Ether (30 ml.) is added and the precipitate filtered off, washed with ether and dried.

PREPARATION E

2-Amino-4-methoxy-6,7-dimethylsulfinylquinoline

A solution of 2-amino-4-methoxy-6,7-dimethylthioquinoline (2 millimoles) in trifluoroacetic acid (4 ml.) is heated to 55° C. on an oil bath. Hydrogen peroxide (452 mg. of 30% H₂O₂, 4 millimoles) is added and the reaction mixture stirred for ten minutes. After cooling to room temperature, absolute ethanol (12 ml.) is added. The resulting precipitate is filtered off, washed with ether and dried. It is recrystallized from ethanol.

What is claimed is:

1. A compound of the formula

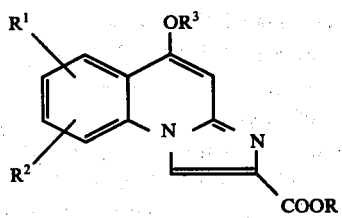

wherein R is hydrogen or alkyl having from one to five carbon atoms;

R¹ and R² are each selected from the group consisting of hydrogen, alkyl having from one to five carbon atoms, alkoxy having from one to five carbon atoms, fluoro, chloro, bromo, methylthio and methylsulfinyl, with the proviso that when both of said R¹ and R² are branched chain alkyl or branched chain alkoxy they are located on nonadjacent position; and when R¹ and R² are taken together they form a member of group consisting of tetramethylene, 1,3-butadienyl, methylenedioxy and ethylenedioxy, each said group being attached to adjacent carbon atoms of said benzenoid ring;

R³ is alkyl having from one to five carbon atoms;

and the pharmaceutically acceptable cationic salts of those compounds wherein R is hydrogen.

2. A compound according to claim 1 wherein R is hydrogen and the pharmaceutically acceptable cationic salts thereof.

3. A compound according to claim 2 wherein each of R¹ and R² is a member selected from the group consisting of hydrogen, alkyl having from one to five carbon atoms, alkoxy having from one to five carbon atoms, fluoro and chloro or R¹ and R² taken together form tetramethylene.

4. A compound according to claim 3 wherein R³ is methyl or ethyl.

5. A compound according to claim 4 wherein R¹ and R² are each hydrogen.

6. The compound according to claim 4 wherein R¹ is hydrogen, R² is 7-fluoro and R³ is ethyl.

7. The compound according to claim 4 wherein R¹ is hydrogen, R² is 8-fluoro and R³ is methyl.

8. The compound according to claim 4 wherein R¹ is hydrogen, R² is 7-chloro and R³ is methyl.

9. A compound according to claim 4 wherein R¹ is hydrogen, and R² is 7-methyl or 7-ethyl.

10. The compound according to claim 4 wherein R¹ is 7-methoxy, R² is 8-methoxy and R³ is methyl.

11. A compound of the formula

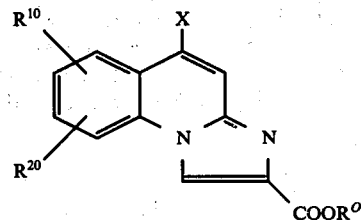

wherein X is chloro or bromo;

R⁰ is alkyl having from one to five carbon atoms;

R¹⁰ and R²⁰ are each selected from the group consisting of hydrogen, alkyl having from one to five carbon atoms, alkoxy having from one to five carbon atoms and fluoro, with the proviso that when both of said R¹⁰ and R²⁰ are branched chain alkyl or branched chain alkoxy they are located on nonadjacent positions; and when R¹⁰ and R²⁰ are taken together they form a member of the group consisting of tetramethylene, 1,3-butadienyl, methylenedioxy and ethylenedioxy, each said group being attached to adjacent carbon atoms of said benzenoid ring.

12. A method of inhibiting the release of mediators of anaphylaxis in a mammalian subject which comprises administering to the subject orally, parenterally or by inhalation, an anaphylaxis mediator release inhibiting amount of a compound having the formula

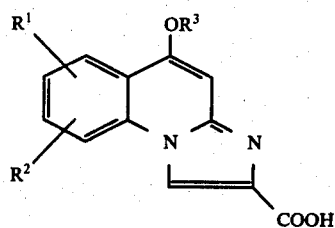

wherein $R^1$ and $R^2$ are each selected from the group consisting of hydrogen, alkyl having from one to five carbon atoms, alkoxy having from one to five carbon atoms, fluoro, chloro, bromo, methylthio and methylsulfinyl, with the proviso that when both of said $R^1$ and $R^2$ are branched chain alkyl or branched chain alkoxy they are located on non-adjacent positions; and when $R^1$ and $R^2$ are taken together they form a member of the group consisting of tetramethylene, 1,3-butadienyl, methylenedioxy and ethylenedioxy, each said group being attached to adjacent carbon atoms of said benzenoid ring;

$R^3$ is alkyl having from one to five carbon atoms;

and the pharmaceutically acceptable cationic salts thereof.

13. The method according to claim 12 wherein $R^1$ and $R^2$ are each hydrogen and $R^3$ is methyl or ethyl.

14. The method according to claim 12 wherein $R^1$ is hydrogen, $R^2$ is 7-fluoro and $R^3$ is ethyl.

15. The method according to claim 12 wherein $R^1$ is hydrogen, $R^2$ is 8-fluoro and $R^3$ is methyl.

16. The method according to claim 12 wherein $R^1$ is hydrogen, $R^2$ is 7-chloro and $R^3$ is methyl.

17. The method according to claim 12 wherein $R^1$ is hydrogen, $R^2$ is 7-methyl or 7-ethyl and $R^3$ is methyl or ethyl.

18. The method according to claim 12 wherein $R^1$ is 7-methoxy, $R^2$ is 8-methoxy and $R^3$ is methyl.

19. A pharmaceutical composition active as an antiallergy agent comprising a pharmaceutically acceptable carrier and a compound of claim 1 wherein R is hydrogen and the pharmaceutically acceptable cationic salts thereof.

20. A pharmaceutical composition as claimed in claim 19 in a form suitable for administration by inhalation.

21. A pharmaceutical composition as claimed in claim 19 comprising a solution or suspension of the antiallergy agent in water.

22. A pharmaceutical composition as claimed in claim 19 comprising a suspension of the antiallergy agent in a liquified propellant.

23. A pharmaceutical composition as claimed in claim 19 comprising the solid antiallergy agent in a solid diluent.

* * * * *